(12) United States Patent  
Davis

(10) Patent No.: US 8,328,357 B2  
(45) Date of Patent: Dec. 11, 2012

(54) VIEWING DEVICE TO MINIMIZE PARALLAX

(76) Inventor: Andrew P. Davis, Bellevue, WA (US)

( * ) Notice: Subject to any disclaimer, the term of this patent is extended or adjusted under 35 U.S.C. 154(b) by 173 days.

(21) Appl. No.: 12/749,323

(22) Filed: Mar. 29, 2010

(65) Prior Publication Data

US 2010/0245768 A1 Sep. 30, 2010

Related U.S. Application Data

(60) Provisional application No. 61/211,271, filed on Mar. 28, 2009.

(51) Int. Cl.
*A61B 3/10* (2006.01)
*A61B 3/00* (2006.01)

(52) U.S. Cl. ........................... 351/215; 351/246
(58) Field of Classification Search ........... 351/200–246
See application file for complete search history.

(56) References Cited

U.S. PATENT DOCUMENTS

| 5,757,461 A * | 5/1998 | Kasahara et al. ............ 351/206 |
| 5,801,807 A * | 9/1998 | Satake et al. ................. 351/221 |
| 6,613,041 B1 * | 9/2003 | Schrunder ........................ 606/5 |

\* cited by examiner

*Primary Examiner* — Mohammed Hasan
(74) *Attorney, Agent, or Firm* — Lowe Graham Jones PLLC

(57) ABSTRACT

A viewing device usable by a surgeon to make an accurate corneal mark during an eye surgery procedure may be a face or head-mounted device to free the surgeon's hands. The device incorporates a light producing apparatus, such as an LED, that may be positioned to be coaxial or otherwise substantially co-aligned with a line-of-sight of the surgeon's dominant eye, and thus match the patient's line of sight with the surgeon's line of sight. The device include polarizing filters that cooperate with the light to minimize or even eliminate parallax viewing of a corneal light reflex by the surgeon's non-dominant or other eye. Further, the device may also include magnification lenses to enhance the view of the eye as seen by the surgeon.

23 Claims, 3 Drawing Sheets

US 8,328,357 B2

VIEWING DEVICE TO MINIMIZE PARALLAX

PRIORITY CLAIM

This application claims the benefit of U.S. Provisional Application No. 61/211,271 filed Mar. 28, 2009, the subject matter of which is incorporated herein in its entirety.

FIELD OF THE INVENTION

This invention relates generally to a viewing device that minimizes parallax and, more specifically, to a head mountable viewing device that minimizes parallax to permit marking of a cornea.

BACKGROUND OF THE INVENTION

The surgical correction of astigmatism has become a common part of cataract surgery. Astigmatic intraocular lenses (IOL) and limbal relaxing incisions (LRI) are the most common methods used in conjunction with cataract surgery to correct the astigmatic error. Before the astigmatic error can be surgically corrected, the surgeon or assistant must mark the cornea to designate the horizontal and vertical axis, or preferably, the astigmatic axis, while the patient is sitting, since the patient's eye rotates slightly when the patient is lying down. Marking the cornea using the corneal light reflex and a gravity assisted astigmatic marker has been described in U.S. Provisional Patent Application No. 61/072,758, the subject matter of which is incorporated herein by reference in its entirety. Because most of the ophthalmic instrumentation for measuring the astigmatic error uses the light reflex, there are theoretical benefits to using the corneal light reflex to mark the cornea for the correction of the astigmatic error.

Using the corneal light reflex to mark the cornea, however presents several challenges. The light reflex on the cornea is actually quite small and dim. Consequently, it can be difficult for the surgeon or assistant to see it. This problem may be exacerbated if the surgeon is presbyopic. One known solution to this problem was recently developed by Mastel Precision out of South Dakota. The solution includes attaching a fixation light to a surgical magnifier worn by the surgeon. The fixation light facilitates marking the cornea when used with the gravity assisted astigmatic marker. Additionally, this solution frees the surgeon's hands so that an assistant is not needed to hold the patient's eyelids when the marks are being made.

SUMMARY OF THE INVENTION

At least one embodiment of the present invention is a viewing device that may be used by a surgeon or surgeon's assistant, for example, to make an accurate corneal mark during an eye surgery procedure. For purposes of this description, the term surgeon will be used, but it is appreciated that the device may be usable by a variety of persons to accomplish the same or similar tasks. The device may be a head-mounted device (e.g., head strap or eye glasses) to free the surgeon's hands, which in turn allows that person to hold the marking instrument and the patient's eyelids without the assistance of another person. The device incorporates a fixation light that may be positioned to be coaxial or otherwise co-aligned with a line-of-sight of the surgeon's dominant eye, and thus match the patient's line of sight with the surgeon's line of sight. The device include polarizing filters that cooperate with the fixation light to minimize or even eliminate parallax viewing of a corneal light reflex by the surgeon's non-dominant or other eye. Further, the device may also include magnification lenses to enhance the view of the eye as seen by the surgeon.

In one aspect of the present invention, an apparatus for marking a cornea of a patient's eye includes a first polarizing filter positioned in a line-of-sight of a first eye of a person prepared to mark the cornea; a light producing apparatus positioned on a first side of the first polarizing filter, the light producing apparatus adjustable to direct light through the first polarizing filter in a desired direction, the directed light becoming a polarized light after passing through the first polarizing filter; and a second polarizing filter positioned in a light line-of-sight of a second eye of the person prepared to mark the cornea, the second polarizing filter configured to substantially block the polarized light reflected from the cornea.

In another aspect of the present invention, a method for marking a cornea of a patient's eye includes the steps of (1) adjusting a direction of a light generated by a light producing apparatus to be in a desired direction, the light producing apparatus coupled to a head mounted viewing device worn by a person prepared to mark the cornea; (2) polarizing the light with a first polarizing filter coupled to the head mounted viewing device; (3) reflecting at least some of the polarized light from the patient's eye; (4) receiving the reflected, polarized light through a second polarizing filter coupled to the head mounted viewing device; and (5) marking a cornea of the patient's eye for purposes of making a surgical incision.

In another aspect of the present invention, a viewing device includes an adjustable head mountable assembly; two polarizing filters positioned adjacent one another, the filters coupled to the head mountable assembly; and a light producing apparatus coupled to the head mountable assembly, the light producing apparatus adjustable to direct light through a first polarizing filter in a desired direction, the directed light becoming a polarized light after passing through the first polarizing filter. Further, the first polarizing filter includes a polarization different than the second polarizing filter such that the polarized light is substantially blocked from travelling through the second polarizing filter after reflecting off of an object.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

As discussed above, attaching a fixation light to a surgical magnifier worn by a surgeon to facilitate marking a cornea with a gravity-assisted astigmatic marker falls short of solving some other problems associated with corneal marking. For example, if the fixation light is attached in the center of the surgical magnifier, it would not be coaxial or substantially co-aligned with either of the surgeon's eyes. In turn, this may introduce error in that the optical axis of the patient is not aligned with the line-of-sight of the surgeon. Moreover, the surgical magnifier does not minimize the issue of parallax, which is generally defined as an apparent change in the direction of an object, caused by a change in observational position that provides a new line of sight. Accordingly, if the surgeon uses both of his eyes to focus on the corneal light reflex, the surgeon would see two marking instruments. But, if the surgeon focuses on the marking instrument then the surgeon would see two light reflexes. Either situation results in confusing images, which reduces the accuracy of the corneal marks. If the surgeon closes one eye to "sight the light reflex" with the marking instrument, the surgeon loses stereopsis, which then makes it difficult to judge how far the marker is from the cornea.

Figure 1:
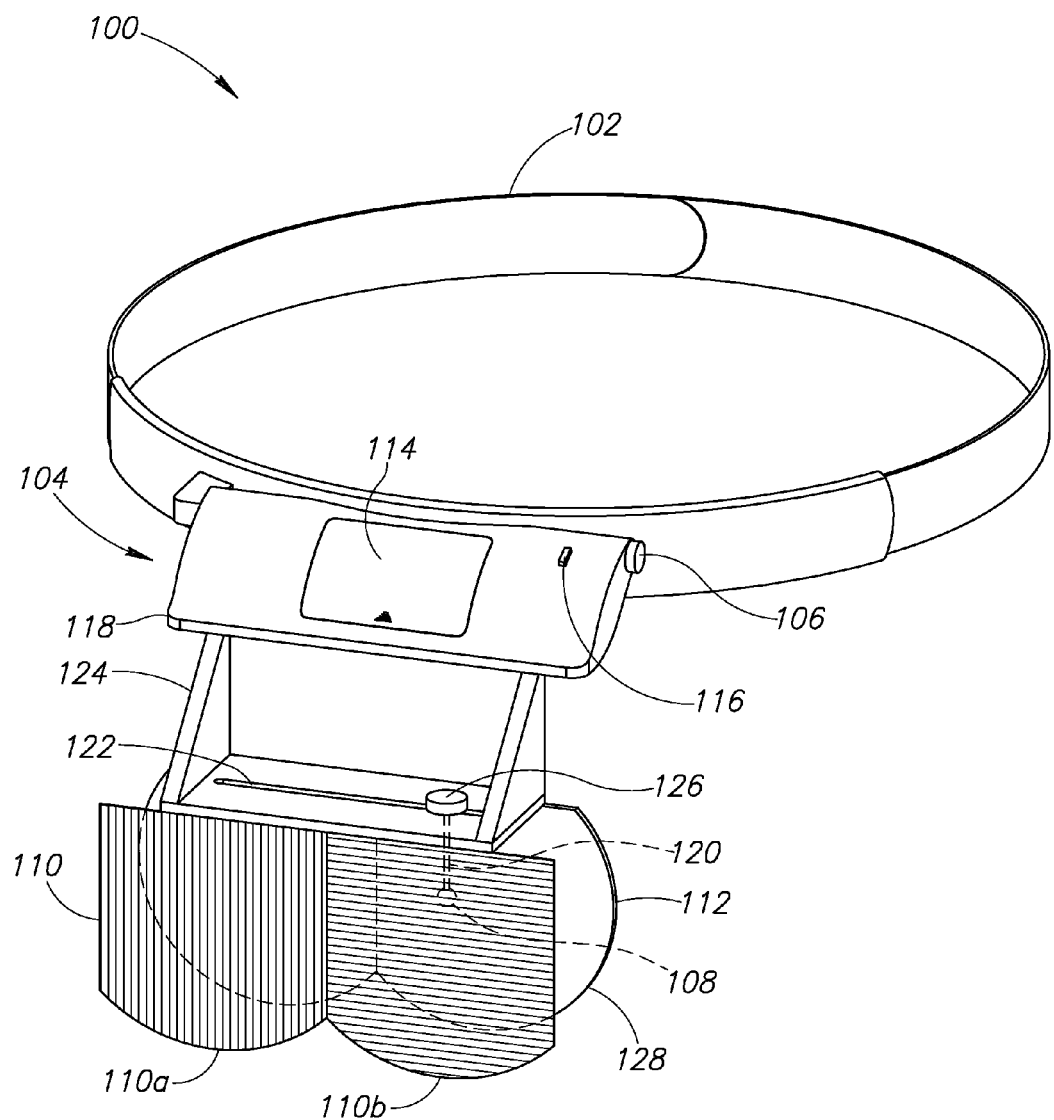
FIG. 1 is a perspective view of a viewing device having a light producing apparatus and a pair of polarizing filters in accordance with an embodiment of the present invention.

FIG. 1 shows a viewing device 100 having an adjustable head strap 102 and lens mounting assembly 104 pivotally coupled with a pin 106 to the head strap 102 according to an embodiment of the present invention. A light producing apparatus 108, which may take the form of a light emitting diode (LED), is coupled and slidably movable relative to the lens mounting assembly 104. A pair of polarizing filters 110 extends from the lens mounting assembly 104 such that they are positioned in a line-of-sight of a wearer. In addition, the viewing device 100 may include one or more magnifying lenses 112 positioned behind the light producing apparatus 108. A battery compartment 114 and an ON/OFF switch 116 for the light producing apparatus 108 may be incorporated into a housing 118 of the lens mounting assembly 104.

Polarization is a property of light waves that describes an orientation of their oscillations. The polarizing filters 110 preferably cooperate with one another such that one of them (e.g., a right filter 110a) blocks nearly all light of one polarization while the other (e.g., a left filter 110b) passes nearly all light of an orthogonal or perpendicular (i.e., right angles) polarization. In an alternative embodiment, other types of polarization, for example, circular polarization, may be used. For purposes of the description herein, polarized light may include fully polarized light, which is light having each and every wave crest oriented in the same direction, but more accurately includes partially polarized light in which one polarization predominates. It is appreciated that even with orthogonally oriented polarizing filters that all polarizations are typically present to some degree.

In the illustrated embodiment, the right polarizing filter 110a and the left polarizing filter 110b have opposite or orthogonal polarizations. Stated otherwise, the direction of polarization of the right side polarizing filter 110a is oriented at ninety degrees from the direction of polarization of the left side polarizing filter 110b (e.g., the orientation of the right side is 90 degrees while the left side is 0 degrees or the right side is 45 degrees while the left side is 135 degrees).

The light producing apparatus 108 is illustrated as a small white LED fixation light 108 and is approximately behind the left side polarizing filter 110b such that a light from the LED may be directed along a visual axis of a patient's left eye (not shown). The light producing apparatus 108 may produce light of any color, but white may advantageously allow for illumination of the patient's eye, as well as making it easier to determine a patient's optical axis. The light producing apparatus 108 is attached to an elongated arm 120 received in a guide channel 122 a frame structure 124 of the lens mounting assembly 104. The arm 120 may be moved along the guide channel 122 so that the light producing apparatus 108 may be positioned in front of either of the surgeon's left or right eye (whichever is dominant), and may also be adjusted for individual variations of the papillary distance. The arm 120 may be secured to the frame 124 with a thumbnut 126, as shown, or another type of securing device (e.g., clip, pin, etc.)

The viewing device 100 may further include a binocular magnifying lens 128 positioned behind the light producing apparatus 108. The binocular magnifying lens may include right and left portions to correspond with the patient's right and left eyes, respectively. In one embodiment the lens 128 takes the form of 2× binocular magnifying lens and is directly attached to the frame 124 of the lens mounting assembly 104. Further, the polarizing filters 110 are aligned with the right and left portions of the lens 128.

Figure 2:
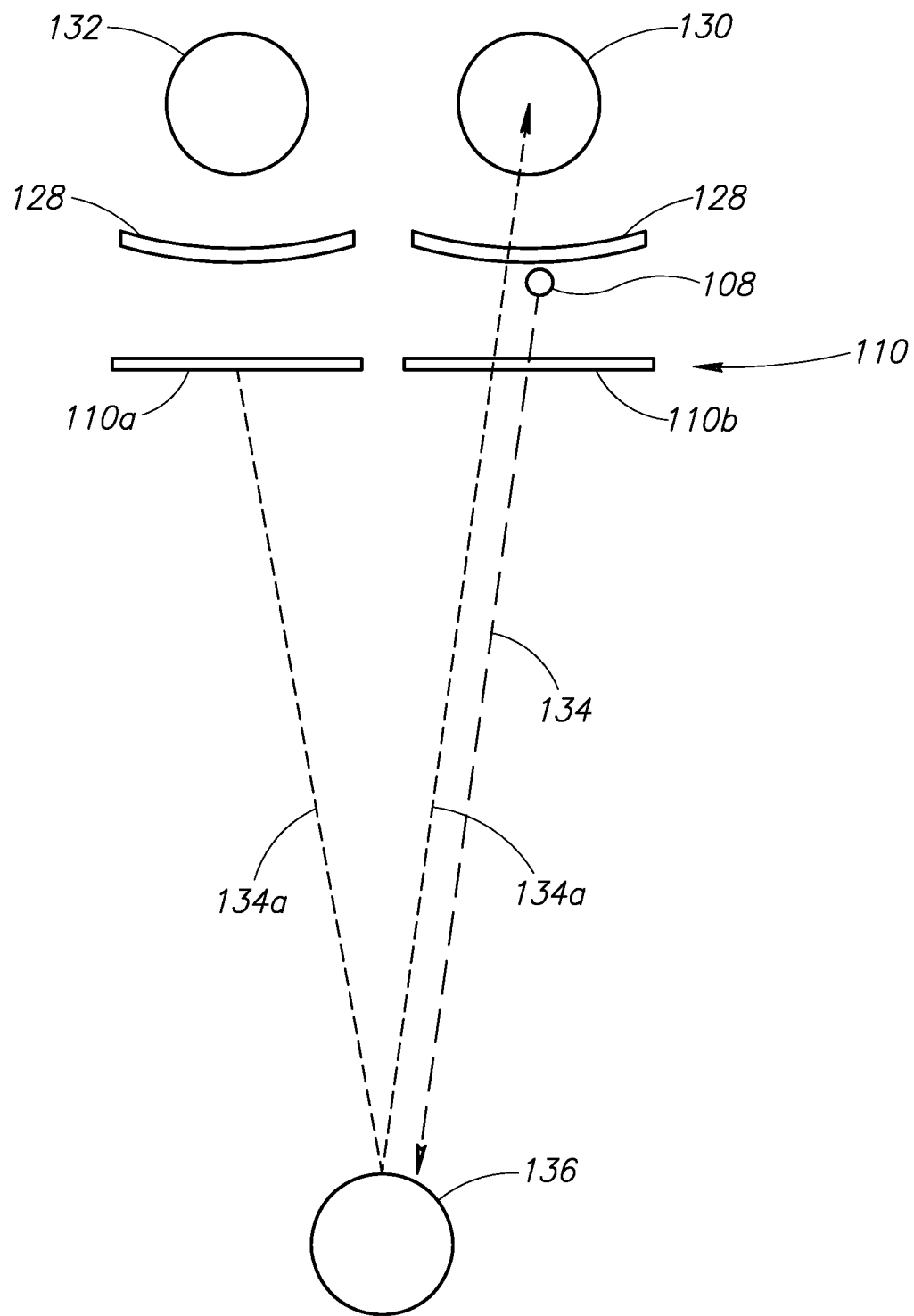
FIG. 2 is a schematic view showing an operation of the viewing device of FIG. 1 in accordance with an embodiment of the present invention.

FIG. 2 shows a schematic diagram of how the polarization filters 110 minimize the parallax condition that may be experienced by a surgeon when making a corneal marking. In the illustrated embodiment, it is merely exemplary that a left eye 130 is the surgeon's dominant eye and a right eye 132 is the non-dominant eye. Because the right and left polarizing filters 110a, 110b are opposite in polarization, like three-dimensional glasses, the light producing apparatus 108 shines through the left side polarizing filter 110b, which polarizes a light 134 directed toward a patient's eye, and more specifically toward a patient's cornea 136. The light 134 reflects off of the cornea 136 and at least some of the polarized light 134a passes back toward the polarizing filters 110 through the magnifying lens or lenses 128. The polarized light 134a reflected back toward the left side polarizing filter 110b may pass through the same and be processed by the surgeon's left eye 130. The polarized light 134a reflected back toward the right side polarizing filter 110a is substantially, if not completely, blocked such that it cannot be seen by the surgeon's right eye 132, which is also not coaxial or substantially co-aligned with a direction of the light 134 as it leaves the light producing apparatus 108.

With the patient looking at the light producing apparatus 108, beaming light 134 that is coaxial or substantially co-aligned with the surgeon's left eye 130, the surgeon can only process light 134a that is reflect back through the left side polarizing filter 110b even though the surgeon is viewing the patient with both eyes. Consequently, even if the surgeon focuses on a marking instrument, there is minimal, if any parallax, which allows the surgeon to make a more accurate corneal marking. In addition, the polarized, reflected light 134a may be magnified by the lens 128 to further assist the surgeon in viewing the patient's eye.

Figure 3:
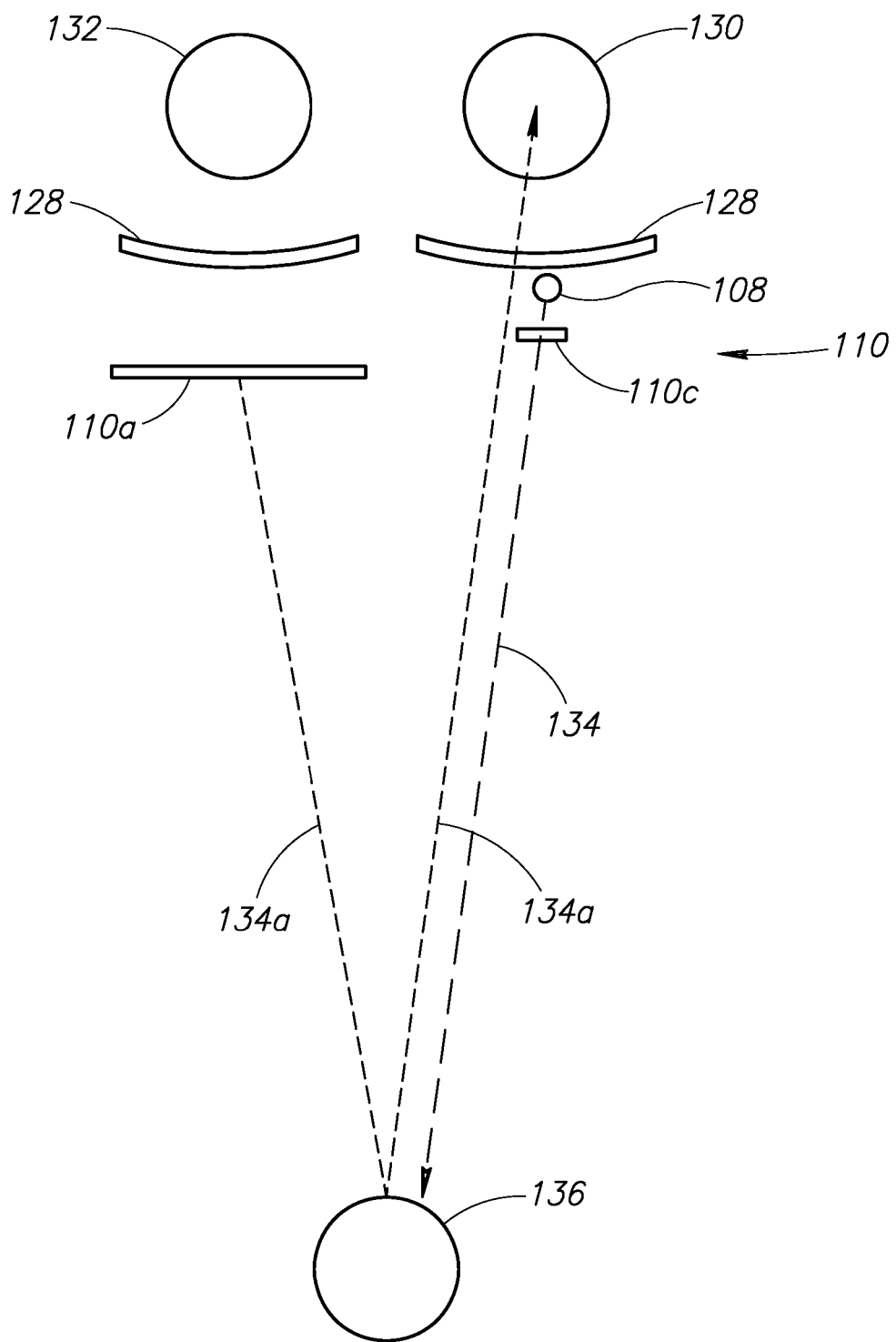
FIG. 3 is a schematic view showing an operation of the viewing device of FIG. 1 in accordance with an alternative embodiment of the present invention.

In yet another embodiment, shown with reference to FIG. 3, a modified polarizing filter 110c may be positioned substantially over the light producing apparatus 108 but not substantially over the surgeon's left eye 130. In yet an alternative embodiment, the apparatus may combine both the modified polarizing filter 110c (shown in FIG. 3) with a polarizing filter 110b (shown in FIG. 2), preferably both having the same polarity.

Referring back to FIG. 1, to use the viewing device 100 the surgeon powers on the light producing apparatus 108 using the switch or button 116. The surgeon adjusts the head strap 102 and lens mounting assembly 104. Then, the surgeon adjusts the light producing apparatus 108 by loosening the thumbnut 126, and moves the arm 120 along the guide channel 122 until the light is coaxial or substantially co-aligned with the surgeon's dominant eye, but not blocking the view of the dominant eye. The position of the light producing apparatus 108 is secured using the thumbnut 126. The patient may then be asked to sit up and look at the light producing apparatus 108. The surgeon uses a corneal marker (not shown), which may take the form of a gravity assisted astigmatic marker, which has the ability of orienting its centration to the corneal light reflex. The surgeon aligns the marker with the corneal light reflex and marks the corneal axis with the marking instrument.

While the preferred embodiment of the invention has been illustrated and described, as noted above, many changes can be made without departing from the spirit and scope of the invention. By way of example, other embodiments may include telescopic surgical loops instead of simple magnifiers. Instead of polarizing filters, other mechanisms may be used to block light to one eye, such as red/green lenses, shutter mechanisms, circular polarization filters, etc. Further embodiments could be applied to the operative microscope or surgical loupes. Another embodiment may include a light source of different shapes and sizes, such as an illuminated "x" or a small ring light, which would give the light reflex a geometric shape and may facilitate centration of the marker and improve illumination at the same time. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. An apparatus for marking a cornea of a patient's eye, the apparatus comprising:
   a light producing apparatus positioned on a first side of a first polarizing filter, the light producing apparatus adjustable to direct light through the first polarizing filter in a direction substantially coaxial with a line-of-sight of a first eye of a person prepared to mark the cornea, the directed light becoming a polarized light after passing through the first polarizing filter; and
   a second polarizing filter positioned in a line-of-sight of a second eye of the person prepared to mark the cornea, the second polarizing filter configured to substantially block the polarized light reflected from the cornea.

2. The apparatus of claim 1, wherein the polarizing filters are coupled to a head mounted device.

3. The apparatus of claim 1, wherein the light producing apparatus includes a light emitting diode.

4. The apparatus of claim 1, further comprising a magnifying lens.

5. The apparatus of claim 1, wherein the first eye is a dominant eye of a person prepared to mark the cornea.

6. The apparatus of claim 1, wherein the light producing apparatus is selectively movable.

7. A method for marking a cornea of a patient's eye, the method comprising:
   adjusting a direction of a light generated by a light producing apparatus to be in a desired direction, the light producing apparatus coupled to a viewing device worn by a person prepared to mark the cornea;
   polarizing the light with a first polarizing filter coupled to the viewing device;
   reflecting at least some of the polarized light from the patient's eye;
   receiving the reflected, polarized light through a second polarizing filter coupled to the viewing device; and
   marking a cornea of the patient's eye for purposes of making a surgical incision.

8. The method of claim 7, further comprising activating the light producing apparatus.

9. The method of claim 7, wherein adjusting the light in the desired direction includes moving the light relative to the viewing device to be substantially coaxial with a line-of-sight of a first eye of a person prepared to mark the cornea.

10. The method of claim 7, further comprising magnifying the cornea of the patient's eye.

11. The method of claim 7, wherein adjusting the direction of the light generated by the light producing apparatus includes adjusting the direction of the light generated by a light emitting diode.

12. A viewing device comprising:
   an adjustable viewing assembly;
   at least two polarizing filters coupled to the viewing assembly; and
   a light producing apparatus coupled to the viewing assembly, the light producing apparatus adjustable to direct light through the first polarizing filter in a desired direction substantially coaxial with a line-of-sight of a first eye of a person prepared to mark the cornea, the directed light becoming a polarized light after passing through the first polarizing filter;
   wherein the first polarizing filter includes a polarization different than the second polarizing filter such that the polarized light is substantially blocked from travelling through the second polarizing filter after reflecting off of an object.

13. The device of claim 12, wherein the viewing assembly comprises a head mountable apparatus.

14. The device of claim 13, wherein the head mountable apparatus is configured to receive a power source for the light producing apparatus.

15. The device of claim 12, wherein the light producing apparatus includes a light emitting diode.

16. The device of claim 12, further comprising a magnifying lens.

17. An apparatus for marking a cornea of a patient's eye, the apparatus comprising:
   a first polarizing filter positioned substantially coaxial with a line-of-sight of a first eye of a person prepared to mark the cornea;
   a light producing apparatus positioned on a first side of the first polarizing filter, the light producing apparatus adjustable to direct light through the first polarizing filter in a desired direction, the directed light becoming a polarized light after passing through the first polarizing filter; and
   a second polarizing filter positioned in a line-of-sight of a second eye of the person prepared to mark the cornea, the second polarizing filter configured to substantially block the polarized light reflected from the cornea.

18. The apparatus of claim 17, wherein the polarizing filters are coupled to a head mounted device.

19. The apparatus of claim 17, wherein the light producing apparatus includes a light emitting diode.

20. The apparatus of claim 17, wherein the first polarizing filter includes a first polarizing property that is oriented with respect to a second polarizing property of the second polarizing filter.

21. The apparatus of claim 17, further comprising a magnifying lens.

22. The apparatus of claim 17, wherein the first eye is a dominant eye of a person prepared to mark the cornea.

23. The apparatus of claim 17, wherein the light producing apparatus is selectively movable.

* * * * *